(12) United States Patent
Hermelin et al.

(10) Patent No.: US 6,569,857 B1
(45) Date of Patent: May 27, 2003

(54) DIETARY SUPPLEMENT

(75) Inventors: Marc S. Hermelin, Glendale, MO (US); R. Saul Levinson, Chesterfield, MO (US)

(73) Assignee: Drugtech Corporation, Wilmington, DE (US)

( * ) Notice: Subject to any disclaimer, the term of this patent is extended or adjusted under 35 U.S.C. 154(b) by 0 days.

(21) Appl. No.: 09/303,689

(22) Filed: May 3, 1999

(51) Int. Cl.[7] .................. A61K 31/50; A61K 31/44; A61K 33/06

(52) U.S. Cl. .............. 514/249; 514/252.14; 514/345; 424/682

(58) Field of Search .............. 514/185, 549, 514/558, 261, 682, 249, 252.14, 345

(56) References Cited

U.S. PATENT DOCUMENTS

| | | |
|---|---|---|
| 4,431,634 A | 2/1984 | Ellenbogen |
| 4,629,625 A | 12/1986 | Gaull |
| 4,710,387 A | 12/1987 | Uiterwaal et al. |
| 4,752,479 A | 6/1988 | Briggs et al. |
| 4,931,441 A | 6/1990 | Lawrence |
| 4,945,083 A | 7/1990 | Jansen, Jr. |
| 4,994,283 A | 2/1991 | Mehansho et al. |
| 5,231,085 A * | 7/1993 | Alexander et al. ............ 514/44 |
| 5,389,657 A | 2/1995 | Madsen |
| 5,494,678 A | 2/1996 | Paradissis et al. |
| 5,514,382 A | 5/1996 | Sultenfuss |
| 5,922,704 A * | 7/1999 | Bland ..................... 514/185 |

OTHER PUBLICATIONS

*Physicians' Desk Reference for Nonprescription Drugs*, (9th Ed., 1998) 712.
*Physicians' Desk Reference*, (51st Ed., 1997) 1427.
*Physicians' Desk Reference*, (51st Ed., 1997) 2753.
Database CAPLUS on STN, (Columbus. OH, USA), No. 91:173855, Ocetkiewicz et al., 'Study of the suitability of premixes in rabbit,' abstract, Rocz. Nauk. Zootech. 1977, 4(2), 161–173, (Polish).
Database Medline on STN, US National Library of Medicine, (Bethesda, MD, USA), No. 86054328, Van Der Spuy, Z. M. 'Nutrition and Reproduction,' abstract, Clinics in Obstetrics and Gynaecology, Sep. 1985, 12(3), 579–604.

* cited by examiner

*Primary Examiner*—Russell Travers
*Assistant Examiner*—Shengjun Wang
(74) *Attorney, Agent, or Firm*—Nath & Associates PLLC; Gary M. Nath

(57) ABSTRACT

The present disclosure relates to novel nutritional compositions and methods for augmenting the possibility of conception while increasing nutritional stores to aid development of healthy embryos and child growth. The nutritional compositions are intended for use by both males and females planning to conceive a child.

19 Claims, No Drawings

DIETARY SUPPLEMENT

BACKGROUND OF THE INVENTION

1. Field of the Invention

The present invention is directed to novel nutritional compositions, particularly nutritional compositions for men and women planning to conceive children, and methods of using said compositions prior to and during pregnancy to augment the possibility of conception occurring and/or increase nutritional stores for aiding the development of healthy embryos and child growth.

2. Description of the Related Art

Infertility is a serious problem in the United States and throughout the world, in both industrialized and unindustrialized nations. In the United States alone, infertility affects an estimated 20 million families (i.e., approximately 20% of all U.S. families). See The Merck Manual, 1768 (16$^{th}$ Ed. 1992). In about 40% of these cases, the infertility is attributable to the male and in about 40–50% of these cases, the infertility is attributable to the female (note: the cause of infertility in about 10–20% of the cases is indeterminate). See McGraw-Hill Encyclopedia of Science and Technology, 17:417 (6$^{th}$ Ed. 1987).

Evidence indicates that the general health of both males and females prior to conception has a direct impact upon the ability to conceive. See Understanding Nutrition, 479–480 (Whitney and Rolfes eds., 6$^{th}$ Ed., 1993). Further, studies of both men and women have shown that the underlying cause of infertility in a marked proportion of individuals may be attributed to a nutritional factor. See Id. In fact, it has been suggested that the inability to reproduce is one of the first signs of imperfect nutrition. See Id.

Infertility in men is primarily associated with low sperm count, decreased sperm motility, sperm agglutination, impotence and ejaculatory disorders. See The Merck Manual, 1768 (16$^{th}$ Ed. 1992). Animal studies suggest that dietary ascorbate (vitamin C) levels directly affect sperm quality and influence male fertility in scurvy-prone vertebrates. It is believed that high concentrations of ascorbic acid in semen play a key role in maintaining the genetic integrity of sperm cells by preventing oxidative damage to sperm DNA. See Dabrowski, "Ascorbic acid protects against male infertility in teleost fish", Experientia, 52(2):97–100 (1996). There is also evidence that daily vitamin C therapy is useful in the treatment and/or mitigation of decreased sperm motility and agglutination. Gonzalez, "Sperm swim singly after vitamin C therapy", JAMA, 249(20):2747, 2751 (1983).

Various studies suggest that vitamin E is also effective in treating male infertility. For example, one study involving the oral dosing of vitamin E over a three month period resulted in a 50 percent increase in spermatozoal zona binding. See Kessopoulou, "A double-blind randomizing placebo cross-over controlled trial using the antioxidant vitamin E to treat reactive oxygen species associated male infertility", Fertil Steril, 64(4): 825–31 (1995). Another study found that treatment of male infertility patients with oral vitamin E significantly decreased malondialdehyde concentrations, high levels of which are indicia of decreased sperm motility. Suleiman, "Lipid peroxidation and human sperm motility: protective role of vitamin E", J Androl, 17(5):530–7 (1996); See also, Vezina, "Selenium-vitamin E supplementation in infertile men. Effects on semen parameters and micronutrient levels and distribution", Bio Trace Elem Res, 53(1–3):65–83 (1996).

Infertility in women is primarily associated with dysfunction of ovulation, abnormal fallopian tube function and low cervical mucus receptivity. The Merck Manual, 1770–1772 (16$^{th}$ Ed. 1992). Infertility in women has also been linked to abnormally low red cell magnesium levels, and such cases have been successfully treated with dietary supplementation of oral magnesium. See Howard, "Red cell magnesium and glutathione peroxidase in infertile women-effects of oral supplementation with magnesium and selenium", Magnes Res, 7(1):49–57 (1994).

For women planning to conceive children, the role of nutrition is not limited to infertility alone. A mother's body provides the environment in which development of the embryo and fetus occur. See Understanding Nutrition, 479–480 (Whitney and Rolfes eds., 6$^{th}$ ed., 1993). Accordingly, a mother's nutritional status prior to conception directly impacts the development of the fetus and embryo and is therefore implicated in the risk of birth defects. See Id.

In particular, during the first 20–25 days of pregnancy, the placenta is not yet formed and fetal circulation is not yet established. Therefore, during this period the fetus is nourished via digested maternal uterine cells and the diffusion of blood exudates. See Schorah, "Importance of Adequate Folate Nutrition in Embryonic and Early Fetal Development," Vitamins and Minerals in Pregnancy and Lactation, 167–176 (Berger, ed., Vol. 16, 1988). Thus, it has been suggested that good nutrient supply is not only required in the very early stages of pregnancy, but also in the preconceptional period. See Id. It is believed that a good nutrient supply during the preconceptional period and first 20 to 25 days of pregnancy (i.e., the "histiotrophic nutritional phase") is necessary to provide optimal concentrations of essential micronutrients to the endometrium, into which the embryo will embed. See Id. Further, inadequate nutrition prior to and at the time of conception causes the placenta, the function of which is to nourish the developing fetus, to develop incorrectly. "Transplacental Nutrient Transfer and Intrauterine Growth Retardation," Nutrition News 50 (1992): 56–57.

Increased occurrences of birth defects have been linked to inadequate nutrition in women at the time of conception. Cases of infants born with neural tube defect (NTD), i.e., spina bifida and anacephaly, have been documented in women with various nutritional deficiencies, primarily low blood folic acid and vitamin C concentrations. Smithells, "Vitamin deficiencies and neural tube defects", Arch Dis Child 51:944–50 (1976).

Various studies point to a correlation between certain vitamin and mineral deficiencies and the etiologies of specific disease states in humans. See, e.g., Diplock, "Antioxidant Nutrients and Disease Prevention: An Overview," Am. J. Clin. Nutr., 53:189–193 (1991); Documenta Giegy Scientific Tables, 457–497 (Diem and Cemtuer eds., 7$^{th}$ ed., 1975). In particular, studies designed to test the causal relationship between specific micronutrient deficiencies and resulting birth defects elucidate a correlation between proper folic acid and vitamin C levels and the reduction in the recurrence of NTD in the instances where women have experienced at least one prior pregnancy resulting in a child with NTD. See Schorah, "Importance of adequate folate ntrition in embryonic and early fetal development", Vitamins and Minerals in Pregnancy and Lactation, 167–176 (Berger, ed., Vol. 16, 1988).

Multi-vitamin and mineral supplements for treating specific medical conditions and as general nutritional supplements to promote and maintain good health have been described in various references. In particular, compositions and methods for optimizing the general health of both men and women by supplementing the daily diet with specific and multi-vitamin compositions are disclosed in the following references.

Jansen, U.S. Pat. No. 4,945,083, describes multi-factor hematinic vitamin preparations which provide $B_{12}$ and folic acid in a one to one ratio in fully effective daily dosage amounts.

Mehansho, U.S. Pat. No. 4,994,283, describes nutritional mineral supplements comprised of iron compounds and calcium compounds in combination with citrates or tartrates, ascorbates, and optionally, fructose, such that the tendency of calcium to inhibit the bioavailability of iron is reduced, and the conjoint bioavailability of these two important minerals is enhanced.

Briggs et al., U.S. Pat. No. 4,752,479 also describes a multi-vitamin and mineral dietary supplement composition for oral administration. The supplement contains one or more divalent dietary mineral components selected from the group consisting of bioavailable calcium and magnesium, optionally in the presence of one or more additional non-ferrous mineral and vitamin components adapted to be released in the upper gastrointestinal tract, and a bioavailable iron component, present in controlled release form and adapted to be slowly released lower in the gastrointestinal tract, and a method of preventing or treating iron deficiency using such compositions. The supplement could contain about 200 mg of bioavailable calcium and 50 mg of bioavailable magnesium.

Lawrence, U.S. Pat. No. 4,931,441, describes a stabilized aqueous leucovorin calcium composition suitable for administration by injection. The solution can contain about 6.35 mg per mL of luecovorin calcium pentahydrate.

Multi-vitamin and mineral dietary vitamin supplements for pregnant and lactating women have also been described. Sultenfess, U.S. Pat. No. 5,514,382, discloses a daily vitamin and mineral supplement for women which provides necessary nutrients to maintain present health as well as positively influence future health. The vitamin and mineral supplement comprises vitamin A, beta-carotene, niacin, riboflavin, pantothenic acid, pyridoxine, cyanocobalamin, biotin, para-aminobenzoic acid, inositol, choline, vitamin C, vitamin D, vitamin E, vitamin K, boron, calcium, chromium, copper, iodine, iron, magnesium, manganese, molybdenum, selenium, zinc, and bioflavonoid. Niacin (vitamin $B_3$) is present to facilitate the production of the majority of sex hormones by dilating blood vessels, lowering cholesterol and maintaining blood circulation.

Paradissis et al., U.S. Pat. No. 5,494,678, disclose multi-vitamin and mineral supplements for pregnant women which are designed for administration during the first, second and third trimesters of pregnancy. The multi-vitamin and mineral supplements are comprised of a regime of pharmaceutically-acceptable calcium compounds including vitamin D, folic acid, vitamin $B_{12}$, vitamin $B_6$, and vitamin $B_1$. These prenatal supplements are specifically tailored to maximize fetal development and maternal health during each trimester of pregnancy.

Guall, U.S. Pat. No. 4,629,625, discloses both vitamin and/or mineral compositions containing taurine and the utilization of these compositions for human nutritional purposes either singularly or as a supplement to other vitamin and mineral regimes. According to the reference, the taurine-containing composition may be used in conjunction with prenatal vitamin supplements for use by pregnant and lactating mothers.

Uiterwaal et al., U.S. Pat. No. 4,710,387, disclose nutritional supplement preparations intended for pregnant and breast-feeding women. The disclosed supplements are based upon milk constituents, including proteins, fats, carbohydrates, calcium, copper, zinc, iodine, iron, vitamin A, vitamin $B_1$, vitamin $B_6$, vitamin C, vitamin $D_3$, vitamin E, niacin and folic acid. The precise adjustments of the constituents of the preparation is determined by the current consumer.

Ellenbogen, U.S. Pat. No. 4,431,634, discloses multimineral dietary supplement compositions of enhanced iron bioavailability containing magnesium and calcium for use in prenatal therapy specifically tailored to combat iron-deficiency anemia.

The *Physicians' Desk Reference for Nonprescription Drugs* describes various vitamin and mineral supplements for use by women. For example, Stuart Prenatal® is a multi-vitamin and mineral supplement for use "before, during and after pregnancy." It provides vitamins equal to 100% or more of the RDA for pregnant and lactating women. See *Physicians' Desk Reference for Nonprescription Drugs*, ($9^{th}$ Ed., 1988) 712.

Materna® prenatal vitamin and mineral tablets are for use "before, during and after pregnancy" and is indicated to provide vitamin and mineral supplementation throughout pregnancy as well as the postnatal period for both lactating and nonlactating mothers. The reference states that Materna® is "useful for improving nutritional status prior to conception." *Physicians' Desk Reference*, ($51^{st}$ Ed., 1997) 1427.

PreCare® prenatal multi-vitamin and mineral supplement film coated caplets are indicated to provide vitamin and mineral supplementation throughout pregnancy and during postnatal period-both for lactating and nonlactating mothers. The reference discloses that PreCare® is "useful for improving nutritional status prior to conception." *Physicians' Desk Reference*, ($51^{st}$ Ed., 1997) 2753.

Methods and compositions for treating infertility have also been described in various references. Madsen, U.S. Pat. No. 5,389,657, discloses methods of treating infertility by administering therapeutically effective amounts of the glutathione stimulator L-2-oxothiazolidine-4-carboxylate or esters thereof to female mammals having fertility problems. According to the reference, the formulation could be used as part of a complete nutritional formulation for satisfying nutritional requirements.

The compositions and methods discussed above are deficient in various respects. First, the compositions are not specifically formulated to address the problem of infertility. Even the above discussed references which recognize the correlation between nutritional status and infertility do not specifically disclose any specific nutritional formulations for treating infertility and do not offer any guidance with regard to formulating specific nutritional compositions for treating infertility. Thus, these references are inadequate with regard to improving the possibility of conception.

Secondly, previously disclosed compositions only provide nutritional components in levels indicated for maintaining general health and are not need-specific formulations which are designed to address the distinct nutritional needs of men and women planning to conceive. Further, even previously disclosed need-based multi-vitamin and mineral supplements are limited to addressing the general nutritional needs of pregnant women, lactating women or nonpregnant, or non-lactating women. Thus, the specific nutritional needs of men and women during the period of time just prior to conception are not addressed by conventional nutritional supplementation.

Thirdly, conventional ovulatory inducing agents or other infertility agents do not utilize vitamins and minerals as active components and are thus not effective in addressing nutritional needs of men and women planning to conceive, or in reducing the risks of birth defects. Further, these agents may increase the risk of birth defects or have other undesirable side effects.

Therefore, there remains a need for specific nutritional formulations which augment the possibility of conception occurring and reduce the risk of birth defects, as well as support general health. Moreover, there is a particular need for formulations which simultaneously augment the possibility of conception and reduce the risk of birth defects to provide a higher degree of patient compliance and minimize the cost to the patients. Additionally, it is desirable to have formulations which specifically address the differing needs of males and females during the period of time prior to conception.

There is also a need for multi-vitamin and mineral supplements which provide a regimen specifically designed to meet the nutritional requirements of males and females planning to conceive by providing the dosages of vitamins and minerals necessary to avoid vitamin or mineral deficiencies, and in particular those deficiencies associated with male and female infertility. It is always desirable to have formulations which minimize the necessity for medications. It is also particularly desirable to have available formulations for addressing infertility which are suitable for men and women seeking to limit their use of medications. Thus, there is a general overall need for a fundamentally new, safe, effective and comprehensive approach to addressing the physiological needs of men and women planning to conceive children.

SUMMARY OF THE INVENTION

The present invention overcomes the deficiencies of currently available approaches to treating male and female infertility. Further, the present invention overcomes the deficiencies of current multi-vitamin and mineral supplements which do not address the specific needs of males and females planning to conceive a child. The present invention overcomes these deficiencies in a safe and effective manner calculated to augment conception, reduce risk of birth defects and generally support the nutritional requirements of developing fetuses and new born infant, as well as contribute to the general health of the mother and father.

The compositions of the invention include critical nutritional components in dosage levels which optimize possibility of conception and fetal development. The compositions are intended for administration during the period commencing prior to at least two weeks before conception.

Specifically, the present invention provides a nutritional composition for administration to an animal, (e.g., human, mammal or any other animal) during the period commencing prior to at least two weeks before conception, to augment the possibility of conception while enhancing nutritional stores for a developing embryo or fetus prior to and during pregnancy. In one embodiment, the nutritional composition of the present invention comprises about 20 mg to 125 mg per 55 kg of body weight of a vitamin $B_6$ compound or derivative thereof; about 0.1 mg to 3 mg per 55 kg of body weight of a folic acid compound or derivative thereof; and a magnesium compound or derivative thereof in an amount ranging from about 25 mg to 400 mg per 55 kg of body weight. The weight ratio of the folic acid compound or derivative thereof to the vitamin $B_6$ compound or derivative thereof is about 0.0024–0.1200:1; and the weight ratio of the magnesium compound or derivative thereof to the vitamin $B_6$ compound or derivative thereof is about 0.2–20:1.

An alternative embodiment of the present invention is a nutritional composition comprising about 20 mg to 125 mg per 55 kg of body weight of a vitamin $B_6$ compound or derivative thereof; and about 0.1 mg to 3 mg per 55 kg of body weight of a folic acid compound or derivative thereof. The weight ratio of the folic acid compound or derivative thereof to the vitamin $B_6$ compound or derivative thereof is about 0.0024–0.1200:1.

Another embodiment of the present invention is a nutritional composition comprising about 20 mg to 125 mg per 55 kg of body weight of a vitamin $B_6$ compound or derivative thereof; and about 100 mg to 1,000 mg per 55 kg of body weight of a calcium compound or derivative thereof. The weight ratio of the calcium compound or derivative thereof to said vitamin $B_6$ compound or derivative thereof is about 0.25–1:1.

A further embodiment of the present invention is a nutritional composition comprising about 20 mg to 125 mg per 55 kg of body weight of a vitamin $B_6$ compound or derivative thereof; about 0.1 mg to 3 mg per 55 kg of body weight of a folic acid compound or derivative thereof; and about 100 mg to 1,000 mg per 55 kg of body weight of a calcium compound or derivative thereof per 55 kg of body weight. The weight ratio of said folic acid compound or derivative thereof to said vitamin $B_6$ compound or derivative thereof is about 0.0024–0.1200:1; and the weight ratio of said calcium compound or derivative thereof to said vitamin $B_6$ compound or derivative thereof is about 0.25–1:1.

An even further embodiment of the invention is a nutritional composition for administration to an animal during a period commencing prior to at least two weeks before conception, which comprises: about 0.1 mg to 3 mg per 55 kg of body weight of a folic acid compound or derivative thereof; about 100 mg to 1,000 mg per 55 kg of body weight of a calcium compound or derivative thereof per 55 kg of body weight; and a magnesium compound or derivative thereof in an amount ranging from about 25 mg to 400 mg per 55 kg of body weight. The weight ratio of said folic acid compound or derivative thereof to said calcium compound or derivative thereof is about 0.0001–0.0300:1.

Another embodiment of the present invention includes a nutritional composition comprising about 20 mg to 125 mg per 55 kg of body weight of a vitamin $B_6$ compound or derivative; about 0.1 mg to 3 mg per 55 kg of body weight of a folic acid compound or derivative thereof; and about 10 mg to 200 mg per 55 kg of body weight of a fatty acid compound selected from the group consisting of a linoleic acid compound, a linolenic acid compound, and derivatives and mixtures thereof. The weight ratio of said folic acid compound or derivative thereof to said vitamin $B_6$ compound or derivative thereof is about 0.0024–0.1200:1. The weight ratio of said fatty acid compound to said vitamin $B_6$ compound or derivative thereof is about 0.08–3.75:1.

Yet another embodiment of the invention provides a nutritional composition comprising about 20 mg to 125 mg per 55 kg of body weight of a vitamin $B_6$ compound or derivative thereof; about 0.1 mg to 3 mg per 55 kg of body weight of a folic acid compound or derivative thereof; and about 10 mg to 500 mg per 55 kg of body weight of a fatty acid compound selected from the group consisting of a docosahexaenoic acid compound, an arachidonic acid compound, and derivatives and combinations thereof. The weight ratio of said folic acid compound or derivative thereof to said vitamin $B_6$ compound or derivative thereof is about 0.0024–0.1200:1; and wherein the weight ratio of said fatty acid compound to said vitamin $B_6$ compound or derivative thereof is about 0.08–25:1.

A further embodiment provides a nutritional composition for administration to an animal during a period commencing prior to at least two weeks before conception to augment the possibility of conception while enhancing nutritional stores for a developing embryo or fetus prior to and during pregnancy. The composition comprises about 0.1 mg to 3 mg per 55 kg of body weight of a folic acid compound or derivative thereof; a magnesium compound or derivative thereof in an amount ranging from about 25 mg to 400 mg per 55 kg of body weight; and a vitamin C compound or derivative thereof in an amount ranging from about 25 mg to 600 mg per 55 kg of body weight.

Yet another further embodiment of the invention provides a nutritional composition, which comprises: about 0.1 mg to 3 mg per 55 kg of body weight of a folic acid compound or derivative thereof; a magnesium compound or derivative thereof in an amount ranging from about 25 mg to 400 mg per 55 kg of body weight; and a vitamin E compound or derivative thereof in an amount ranging from about 10 I.U. to 400 I.U. per 55 kg of body weight.

The present invention also includes methods for augment the possibility of conception while enhancing nutritional stores for a developing embryo or fetus prior to and during pregnancy. In one embodiment, the methods of the present invention include administering to an animal during a period commencing prior to at least two weeks before conception a composition comprising about 20 mg to 125 mg per 55 kg of body weight of a vitamin $B_6$ compound or derivative thereof; about 0.1 mg to 3 mg per 55 kg of body weight of a folic acid compound or derivative thereof. The weight ratio of said folic acid compound or derivative thereof to said vitamin $B_6$ compound or derivative thereof is about 0.0024–0.1200:1.

In an alternative embodiment of the invention, a method is provided for increasing the possibility of conception while enhancing nutritional stores for a developing embryo or fetus prior to and during pregnancy, which comprises administering to an animal during a period commencing prior to at least two weeks before conception a composition comprising: about 20 mg to 125 mg per 55 kg of body weight of a vitamin $B_6$ compound or derivative thereof; and about 100 mg to 1,000 mg per 55 kg of body weight of a calcium compound or derivative thereof. The weight ratio of said calcium compound or derivative thereof to said vitamin $B_6$ compound or derivative thereof is about 0.25–1:1.

In another embodiment, a method is provided, which comprises administering to an animal during a period commencing prior to at least two weeks before conception a composition including about 20 mg to 125 mg per 55 kg of body weight of a vitamin $B_6$ compound or derivative thereof; about 0.1 mg to 3 mg per 55 kg of body weight of a folic acid compound or derivative thereof; about 100 mg to 1,000 mg per 55 kg of body weight of a calcium compound or derivative thereof. The weight ratio of said folic acid compound or derivative thereof to said vitamin $B_6$ compound or derivative thereof is about 0.024–0.1200:1; and the weight ratio of said calcium compound or derivative thereof to said vitamin $B_6$ compound or derivative thereof is about 0.25–1:1.

In a further embodiment of the invention, a method is provided, which comprises administering to a male animal and a female animal during a period commencing prior to at least two weeks before conception a composition comprising a nutritional agent selected from the group consisting of a vitamin $B_6$ compound, a folic acid compound, a magnesium compound, a vitamin C compound, a vitamin E compound, a derivative thereof and a mixture thereof; wherein said male and said female animal are attempting to conceive a child together.

In a still further embodiment of the invention, a method is provided, which comprises: administering to an animal during a period commencing prior to at least two weeks before conception a composition comprising: about 0.1 mg to 3 mg per 55 kg of body weight of a folic acid compound or derivative thereof; and about 100 mg to 1,000 mg per 55 kg of body weight of a calcium compound or derivative thereof.

Thus, the inventive subject matter addresses the specific needs of men and women attempting to conceive through novel compositions and methods. Additional features and advantages of the present invention are described in, and will be apparent from, the detailed description of the presently preferred embodiments.

DETAILED DESCRIPTION OF THE INVENTION

As used herein, "infertility" refers to the difficulty or inability to conceive during the course of normal sexual activity, when one year of unprotected intercourse has elapsed without a resulting conception.

"Animal" refers to a human, mammal or any other animal.

"Conception" refers to the beginning of pregnancy as marked by the formation of a zygote.

"Possibility of conception" refers to the likelihood of conception occurring during normal sexual activity.

"Nutritional stores" refers to the levels of vitamins, minerals and other nutrients which will be available for use by the father, mother, developing embryo, fetus and newborn infant.

"Nutritional status" refers to the presence or absence of any vitamin or mineral deficiency, or in other words, the extent to which physiological vitamin and mineral demands are being satisfied such that deficiency is avoided.

The present invention is based, in part, upon the discovery that nutritional requirements vary throughout an individual's lifetime and as a result of various external and internal factors. In particular, certain factors heighten the physiological demand for certain vitamins, minerals and other nutrients and components. Moreover, in some circumstances certain nutritional agents have positive benefits beyond their usual function of maintaining health.

The present inventive subject matter recognizes that there are substantial physiological benefits attained by specifically formulating multi-vitamin and mineral supplements for use by males and females planning to conceive children. Further, the nutritional needs of persons planning to conceive children are different from the nutritional needs of males and females who are not planning to conceive. The products of the invention provide optimum nutritional components and amounts which have been found to alleviate nutritional causes of infertility and provide for optimal health prior to conception.

Without being limited by theory, the compositions and methods of the present invention may be effective because they prevent deficiencies of vitamins, minerals and other nutrients which are necessary to conception. Alternatively, the compositions and methods may be effective because they initiate, stimulate or act as catalysts to reactions having a positive impact on the processes of conception and fetal development.

The multi-vitamin and mineral supplements of the present invention contain specific concentrations of vitamin and minerals for administration to males and females prior to conception to alleviate vitamin and mineral deficiencies which may cause infertility. The present invention also satisfies specific vitamin and mineral requirements, the absence of which have been found to cause birth defects, as well as to provide for general health after conception and during the resultant pregnancy. The formulations of the invention optimize the nutritional benefits of supplementation as required by the physiological stresses of conception.

The nutritional compositions of the present invention are formulated for administration to humans and other animals during the period prior to and including conception. The effectiveness of the compositions appears to increase in relationship to the length of time between initiation of use and time of conception. Preferably, the compositions are administered during the period commencing prior to at least two weeks before conception. More preferably, the compositions are administered during the period commencing prior to at least four weeks before conception. Even more preferably, the compositions are administered during the period commencing prior to at least twelve weeks prior to conception. Most preferably, the compositions are administered during the period of time commencing prior to at least six months prior to conception.

The nutritional compositions are formulated to augment the possibility of conception. The extent to which the possibility of conception is increased by use of the formulas may be influenced by numerous external factors, such as the following non-limiting examples: stress, alcohol consumption, drug use, poor compliance, and the like. Moreover, the effectiveness of the compositions may vary from individual to individual, and from couple to couple, for an wide array of reasons, such as genetic predisposition, health factors, and the like, without limitation.

While it is difficult to quantify the likelihood of conception, the average healthy couple may be able to augment conception through use of the present formulations. Moreover, even for couples that could not be classified as average healthy couples, the possibility of conception may be augmented, particularly where the formulations directly impact upon the factor causing the abnormality.

The formulations of the present invention can contain vitamin $B_6$ or derivatives thereof. Derivatives of vitamin $B_6$ include compounds formed from vitamin $B_6$ which are structurally distinct from vitamin $B_6$, but which retain the active function of vitamin $B_6$. Such derivatives include, without limitation, salts of vitamin $B_6$, chelates of vitamin $B_6$, combinations thereof and the like. The vitamin $B_6$ may be present in a single form or in various different forms in combination within the present compositions. The specific amount of vitamin $B_6$ in the compositions is adjusted based on the type of dosage form utilized (i.e., immediate release vs. controlled release). In the case of the immediate release compositions, the amounts of vitamin $B_6$ in the compositions preferably range from about 10 mg to about 75 mg per 55 kg of body weight. More preferably, the amounts of vitamin $B_6$ in the immediate release compositions range from about 15 mg to about 50 mg per 55 kg of body weight. Even more preferably, the amounts of vitamin $B_6$ in the immediate release compositions range from about 17 mg to about 25 mg per 55 kg of body weight. Most preferably, the amounts of vitamin $B_6$ in the immediate release compositions range from about 19 mg to about 21 mg.

The amount of vitamin $B_6$ present in the controlled release compositions of the present invention, preferably range from about 20 mg to about 150 mg per 55 kg of body weight. More preferably, the amounts of vitamin $B_6$ present in the controlled release compositions range from about 70 mg to about 125 mg.

The compositions of the present invention may include a folic acid compound or derivative thereof. The derivatives of folic acid include compounds formed from folic acid which are structurally distinct from folic acid, but which retain the active function of folic acid. Non-limiting examples of such derivatives include salts of folic acid, chelates of folic acid, combinations thereof and the like. Preferably, the amounts of folic acid in the immediate release compositions of the invention range from about 0.1 mg to 3 mg per 55 kg of body weight of a folic acid compound or derivative thereof. More preferably, the amounts of folic acid in the invention range from about 0.5 to about 1 mg per 55 kg of body weight. The amounts of folic acid in the controlled release compositions of the invention preferably range from about 2 mg to about 4 mg per 55 kg of body weight. More preferably, the amounts of folic acid in the controlled release compositions range from about 2.5 to about 3.0 mg per 55 kg of body weight.

A magnesium compound or derivative thereof may be incorporated into the compositions of the present invention. Preferably, the amounts of magnesium in the compositions range from about 10 mg to about 500 mg per 55 kg of body weight. More preferably, the magnesium is in an immediate release form and is present in amounts ranging from about 15 mg to about 125 mg per 55 kg of body weight. Even more preferably, the magnesium is present in a controlled release form in amounts ranging from about 350 mg to about 450 mg per 55 kg of body weight.

The compositions of the present invention may optionally include a vitamin C compound or derivative thereof. The vitamin C is preferably present in the compositions in amounts ranging from about 5 mg to about 2000 mg per 55 kg of body weight. More preferably, the vitamin C is present in the compositions in amounts ranging from about 60 mg to about 1000 mg per 55 kg of body weight. Even more preferably, the vitamin C is present in a controlled release form in amounts ranging from about 300 mg to about 600 mg per 55 kg of body weight.

The present invention may also additionally include a vitamin E compound or derivative thereof. The vitamin E compound or derivative thereof is preferably present in the compositions in an amount ranging from about 10 I.U. to about 600 I.U. per 55 kg of body weight. More preferably, the vitamin E compound or derivative thereof is present in the compositions in an immediate release form in an amount ranging from about 5 mg to about 50 mg per 55 kg of body weight. Even more preferably, the vitamin E compound or derivative thereof is present in the compositions in an immediate release form in an amount ranging from about 10 mg to about 30 mg per 55 kg of body weight. Most preferably, the vitamin E compound or derivative thereof is present in the compositions in a controlled release form in an amount ranging from 350 mg to 450 mg per 55 kg of body weight.

The compositions of the present may contain a calcium compound or derivative thereof. The calcium is preferably present in amounts of about 50 mg to about 1,500 mg per 55 kg of body weight. More preferably, the calcium is present in an immediate release form in amounts of about 75 mg to about 1200 mg per 55 kg of body weight. Even more preferably, the calcium is present in an immediate release form in amounts ranging from about 150 mg to about 1000 mg per 55 kg of body weight. Still more preferably the calcium is in a chewable form in amounts ranging from about 75 mg to about 500 mg per 55 kg of body weight.

The compositions of the present invention optionally contain linoleic acid, linolenic acid, or derivatives or mixtures thereof. Preferably, the linoleic acid, linolenic acid or combination thereof is present in amounts of about 5 mg to 250 mg per 55 kg of body weight. More preferably, the linoleic acid, linolenic acid or combination thereof is present in an immediate release form in an amount of ranging from about 5 mg to about 20 mg per 55 kg of body weight. Even more preferably, the linoleic acid, linolenic acid or combination thereof is presenL in a controlled release form in an amount ranging from about 150 mg to 250 mg per 55 kg of body weight.

The compositions of the present invention may further optionally include docosahexaenoic acid, arachidonic acid or about 10 mg to 200 mg per 55 kg of body weight of a fatty acid compound selected from the group consisting of a docosahexaenoic acid compound, a arachidonic acid compound, and derivatives and mixtures thereof.

Preferred embodiments of the present invention may additionally include a fertility agent, including without limitation, chorionic gonadotropin, clomiphene, gonadorelin, and menotropins.

Particularly, preferred embodiments of the present invention may also further contain one or more ovulatory agents, including without limitation, chorionic gonadotropin, clomiphene, gonadorelin, recombinant human luteinizing hormone, menotropins, progesterone, urofollitropin and combinations thereof.

The weight ratios of various components in the invention are calculated to provide optimal formulations for achieving the objectives of the invention. The weight ratio of the magnesium compound or derivative thereof to said vitamin $B_6$ compound or derivative thereof in the present invention is preferably about 0.2–20:1. More preferably, the weight ratio of said magnesium compound or derivative thereof to said vitamin $B_6$ compound or derivative thereof is about 0.5–10:1. Even more preferably, the weight ratio of the magnesium compound or derivative thereof to the vitamin $B_6$ compound or derivative thereof is about 0.9–5:1.

The weight ratio of folic acid to $B_6$ in the present compositions is preferably about 0.0024–0.1200:1. More preferably, the weight ratio of folic acid to $B_6$ in the present compositions is about 0.0010–0.1100:1. Even more preferably, the weight ratio of folic acid to $B_6$ in the present compositions is about 0.05–0.09:1. Most preferably, the weight ratio of folic acid to $B_6$ is 0.02–0.08:1.

The weight ratio of the calcium compound or derivative thereof to said vitamin $B_6$ compound or derivative thereof in the present invention is preferably about 0.25–1:1. More preferably, the weight ratio of calcium to vitamin $B_6$ is 0.40–0.90:1. Even more preferably, the weight ratio of calcium to vitamin $B_6$ is 0.06–0.8:1.

The weight ratio of the linoleic acid, linolenic acid, or derivatives thereof or mixtures thereof to the vitamin $B_6$ compound or derivative thereof in the present invention is preferably about 0.08–3.75:1. More preferably, the weight ratio of the linoleic acid, linolenic acid, or derivatives thereof or mixtures thereof to the vitamin $B_6$ compound or derivative thereof in the present invention is 0.15–2.50:1. More preferably, the weight ratio of the linoleic acid, linolenic acid, or derivatives thereof or mixtures thereof to the vitamin $B_6$ compound or derivative thereof in the present invention is 0.1–1.0:1. Even more preferably, the weight ratio of the linoleic acid, linolenic acid, or derivatives thereof or mixtures thereof to the vitamin $B_6$ compound or derivative thereof in the present invention is 0.5–0.9:1.

The weight ratio of the docosahexaenoic acid compound, arachidonic acid compound, or derivatives thereof or mixtures thereof to the vitamin $B_6$ compound or derivative thereof in the present invention is preferably about 0.08–25:1. More preferably, the weight ratio of the docosohexaenoic acid compound, arachidonic acid compound, or derivatives thereof or mixtures thereof to the vitamin $B_6$ compound or derivative thereof in the present invention is 1–10:1. Even more preferably, the weight ratio of the docosahexaenoic acid compound, arachidonic acid compound, or derivatives thereof or mixtures thereof to the vitamin $B_6$ compound or derivative thereof in the present invention is 2–8:1. Most preferably, the weight ratio of the docosahexaenoic acid compound, arachidonic acid compound, or derivatives thereof or mixtures thereof to the vitamin $B_6$ compound or derivative thereof in the present invention is 4–6:1.

Magnesium compounds which may be incorporated into the present invention include, but are not limited to, magnesium stearate, magnesium carbonate, magnesium oxide, magnesium hydroxide, and magnesium sulfate.

Calcium compounds which may be incorporated into the present invention include, but are not limited to, any of the well known calcium supplements, such as calcium carbonate, calcium sulfate, calcium oxide, calcium hydroxide, calcium apatite, calcium citrate-malate, bone meal, oyster shell, calcium gluconate, calcium lactate, calcium phosphate, calcium levulinate, and the like.

The fatty acids of the present invention may be from any source, including, without limitation, seed oils, fish oil, canola oil, vegetable oil, safflower oil, sunflower oil, olive oil, soybean oil, corn oil, peanut oil, cottonseed oil, chicken fat, lard, palm oil beef tallow butter, palm kernel oil coconut oil, flaxseed oil and evening primrose oil. Non-limiting exemplary fish oil sources include tuna oil, mackerel oil and salmon oil.

It is also possible in the nutritional composition of the present invention for the dosage form to combine various forms of release, which include, without limitation, immediate release, extended release, pulse release, variable release, controlled release, timed release, sustained release, delayed release, long acting, and combinations thereof. The ability to obtain immediate release, extended release, pulse release, variable release, controlled release, timed release, sustained release, delayed release, long acting characteristics and combinations thereof is performed using well known procedures and techniques available to the ordinary artisan. Each of these specific techniques or procedures for obtaining the release characteristics does not constitute an inventive aspect of this invention.

Any pharmaceutically-acceptable dosage form, and combinations thereof, are contemplated by the invention. Examples of such dosage forms include, without limitation, a chewable tablet, a quick dissolve tablet, an effervescent tablet, reconstitutable powder, elixir, liquid, solution, suspension, emulsion, tablet, multi-layer tablet, bi-layer tablet, capsule, soft gelatin capsule, hard gelatin capsule, caplet, lozenge, chewable lozenge, bead, powder, granules, dispersible granules, cachets, douche, suppository, cream, topical, inhalant, aerosol inhalant, patch, particle inhalant, implant, depot implant, ingestible, injectable, infusion, a health bar, a liquid, a food and combinations thereof. The preparation of any of the above dosage forms is well known in the art.

The following represent examples, without limitation, of acceptable methods of preparing some of the above-listed dosage forms. For example, animal feed may be by methods well known to persons of ordinary skill in the art. Animal feeds may be prepared by mixing the formulation with binding ingredients to form a plastic mass. The mass is then extruded under high pressure to form tubular (or "spaghetti-like") structures that are cut to pellet size and dried.

Quick dissolve tablets may be prepared, for example, without limitation, by mixing the formulation with agents such as sugars and cellulose derivatives, which promote dissolution or disintegration of the resultant tablet after oral administration, usually within 30 seconds.

Cereal coatings may be prepared, for example, without limitation, by passing the cereal formulation, after it has been formed into pellets, flakes, or other geometric shapes, under a precision spray coating device to deposit a film of active ingredients, plus excipients onto the surface of the formed elements. The units thus treated are then dried to form a cereal coating.

For example, health bars may be prepared, without limitation, by mixing the formulation plus excipients (e.g., binders, fillers, flavors, colors, etc.) to a plastic mass consistency. The mass is then either extended or molded to form "candy bar" shapes that are then dried or allowed to solidify to form the final product.

Soft gel or soft gelatin capsules may be prepared, for example, without limitation, by dispersing the formulation in an appropriate vehicle (vegetable oils are commonly used) to form a high viscosity mixture. This mixture is then encapsulated with a gelatin based film using technology and machinery known to those in the soft gel industry. The industrial units so formed are then dried to constant weight.

Chewable tablets, for example, without limitation, may be prepared by mixing the formulations with excipients designed to form a relatively soft, flavored, tablet dosage form that is intended to be chewed rather than swallowed. Conventional tablet machinery and procedures, that is both direct compression and Granulation, i.e., or slugging, before compression, can be utilized. Those individuals involved in pharmaceutical solid dosage form production are well versed in the processes and the machinery used as the chewable dosage form is a very common dosage form in the pharmaceutical industry.

Film coated tablets, for example, without limitation, may be prepared by coating tablets using techniques such as rotating pan coating methods or air suspension methods to deposit a contiguous film layer on a tablet. This procedure is often done to improve the aesthetic appearance of tablets, but may also be done to improve the swallowing of tablets, or to mask an obnoxious odor or taste, or to improve to usual properties of an unsightly uncoated tablet.

Compressed tablets, for example, without limitation, may be prepared by mixing the formulation with excipients intended to add binding qualities to disintegration qualities. The mixture is either directly compressed or granulated then compressed using methods and machinery quite well known to those in the industry. The resultant compressed tablet dosage units are then packaged according to market need, i.e., unit dose, rolls, bulk bottles, blister packs, etc.

The present invention contemplates nutritional compositions formulated for administration by any route, including without limitation, oral, buccal, sublingual, rectal, parenteral, topical, inhalational, injectable and transdermal. The physicochemical properties of nutritional compositions, their formulations, and the routes of administration are important in absorption. Absorption refers to the process of nutritional composition movement from the site of administration toward the systemic circulation. Most orally administered nutritional compositions are in the form of tablets or capsules primarily for convenience, economy, stability, and patient acceptance. They must disintegrate and dissolve before absorption can occur. Using the present invention with any of the above routes of administration or dosage forms is performed using well known procedures and techniques available to the ordinary skilled artisan.

The present invention contemplates the use of pharmaceutically acceptable carriers which may be prepared from a wide range of materials. Without being limited thereto, such materials include diluents, binders and adhesives, lubricants, plasticizers, disintegrants, colorants, bulking substances, flavorings, sweeteners and miscellaneous materials such as buffers and adsorbents in order to prepare a particular medicated composition.

Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches, and derivatives, as well as other conventional binders well known to persons skilled in the art. Exemplary non-limiting solvents are water, ethanol, isopropyl alcohol, methylene chloride or mixtures and combinations thereof. Exemplary non-limiting bulking substances include sugar, lactose, gelatin, starch, and silicon dioxide.

The plasticizers used in the dissolution modifying system are preferably previously dissolved in an organic solvent and added in solution form. Preferred plasticizers may be selected from the group consisting of diethyl phthalate, diethyl sebacate, triethyl citrate, cronotic acid, propylene glycol, butyl phthalate, dibutyl sebacate, caster oil and mixtures thereof, without limitation. As is evident, the plasticizers may be hydrophobic as well as hydrophilic in nature. Water-insoluable hydrophobic substances, such as diethyl phthalate, diethyl sebacate and caster oil are used to delay the release of water-soluble vitamins, such as vitamin $B_6$ and vitamin C. In contrast, hydrophilic plasticizers are used when water-insoluble vitamins are employed which aid in dissolving the encapsulated film, making channels in the surface, which aid in nutritional composition release.

The dosage forms of the present invention may involve the administration of a nutritional composition in a partial, i.e., fractional dose, one or more times during a 24 hour period, a single dose during a 24 hour period of time, a double dose during a 24 hour period of time, or more than a double dose during a 24 hour period of time. Fractional, double or multiple doses may be taken simultaneously or at different times during the 24 hour period.

The compositions of the present invention are intended for use by humans and other animals, and both males and females. The dosages are adjusted according to body weight and thus are set forth herein on a per body weight basis. For example, if the formula specifies a range of 20–125 mg for a 55 kg individual, that range would be adjusted for a 35 kg individual to 13–80 mg (e.g., the lower range limit=(35 kg/55 kg)*20 mg=12.6 mg, or about 13 mg). Decimal amount may be rounded to the nearest whole number. In the above manner, the present compositions may be thus adapted to be suitable for any individual, including any animal, regardless of size.

Moreover, the formulations can be further adapted based upon the specific needs, genetic predispositions or identified deficiencies of the individual planning to conceive. Moreover, the present compositions can be used as one component of a prescribed therapy. Preferably, the compositions are used by both the male and female planning to conceive a child together.

Pharmaceutically acceptable calcium compounds include, but are not limited to, any of the well known calcium supplements, such as calcium carbonate, calcium sulfate, calcium oxide, calcium hydroxide, calcium apatite, calcium citrate-malate, bone meal, oyster shell, calcium gluconate, calcium lactate, calcium phosphate, calcium levulinate, and the like.

The present invention includes methods for increasing the possibility of conception while improving the nutritional stores of the mother prior to conception and enhancing nutritional stores for a developing embryo or fetus prior to and during pregnancy. The methods of the invention comprise administering to a male or a female during a period commencing prior to at least two weeks before conception a composition comprising a vitamin $B_6$ compound, a folic acid compound, a magnesium compound, a calcium compound, a vitamin C compound, a vitamin E compound, a derivative thereof and a mixture thereof. Preferably, the methods of the invention comprise administering the above described composition to both a male and a female planning to conceive a child together. More preferably, the methods of the invention comprise administering any of the above described compositions to males and/or females.

In one preferred embodiment of the invention, the compositions of the invention are provided to a male or female in a blister pack. In a particularly preferred embodiment of the invention, the multi-vitamin and mineral supplements described above are provided to both a male and female in a blister pack with indicia identifying which supplement is for the male and which supplement is for the female, where the male and female are planning to conceive a child together. All of the compositions of the present invention may further include or be accompanied by indicia allowing men and women to identify the compositions as products for persons planning to conceive children.

The methods of the invention may involve the administration of a nutritional composition in a single dose during a 24 hour period of time, a double dose during a 24 hour period of time, or more than two dose during a 24 hour period of time. The dose may be taken simultaneously or at different times depending upon the prescribed dose.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention. The following examples are illustrative of preferred embodiments of the invention and are not to be construed as limiting the invention thereto.

EXAMPLES

Preparation of Nutritional Conception Compositions

Example 1

The following compositions are used to prepare nutritional conception products for administration to men and women during a period commencing prior to at least two weeks before conception:

TABLE I

| COMPONENT | FORMULA I | CHEWABLE FORMULA | CONTROLLED RELEASE |
|---|---|---|---|
| Vitamin E, I.U. | 10–100 | 10–100 | 100–400 |
| Vitamin C, mg | 25–100 | 25–100 | 100–2,000 |
| Vitamin $B_6$, mg | 20–75 | 20–75 | 75–125 |
| Folic Acid, mg | 0.1–1.5 | 0.1–1.5 | 1.5–3 |
| Calcium, mg | 100–300 | 100–300 | 300–1,500 |
| Magnesium, mg | 25–100 | 25–100 | 100–400 |
| Linolenic Acid, mg | 10–100 | — | 100–200 |
| Linoleic Acid, mg | 10–100 | — | 100–200 |
| Docosahexaenoic Acid, mg | 10–500 | — | 10–500 |

Tablets incorporating the above formulations are prepared using conventional methods and materials known in the pharmaceutical art. The resulting nutritional conception composition tablets were recovered and stored for future use.

Example II

The following compositions are used to prepare nutritional conception products for administration during a period commencing prior to at least two weeks before conception:

TABLE II

| Component (in mg unless otherwise indicated) | Formula I | Chewable Formula | Controlled Release |
|---|---|---|---|
| Beta Carotene I.U. | 3,000 | 5,000 | 3,000 |
| Vitamin E, I.U. | 30 | 10 | 400 |
| Vitamin C, | 60 | 25 | 600 |
| Vitamin $B_1$ | 3.0 | 3 | 3 |
| Vitamin $B_2$ | 3.4 | 3.4 | 3.4 |
| Vitamin $B_3$ | 20 | 20 | 20 |
| Vitamin $B_6$ | 20 | 20 | 125 |
| Vitamin $B_{12}$, mcg | 12 | 12 | 12 |
| Folic Acid | 1 | 1 | 3 |
| Calcium | 200 | 100 | 1,000 |
| Elemental Iron | 30 | 30 | 30 |
| Copper | 2 | 2 | 2 |
| Zinc | 15 | 15 | 15 |
| Magnesium | 100 | 25 | 400 |
| Microcrystalline Cellulose | 180 | 180 | — |
| Croscarmellose Sodium | 15 | — | — |
| Stearic Acid | 65 | — | — |
| Mg Stearate | 9 | 9 | 10 |
| Linolenic Acid | 10 | — | 200 |
| Linoleic Acid | 10 | — | 200 |
| Docosahexaenoic Acid | 500 | — | 10 |
| Ethyl Cellulose | — | — | 150 |

Tablets incorporating the above formulations are prepared using conventional methods and materials known in the pharmaceutical art. The resulting nutritional conception composition tablets are recovered and stored for future use.

Example III

The following compositions are used to prepare nutritional conception products for administration during a period commencing prior to at least two weeks before conception:

TABLE III

| COMPONENT | PER 35 KG OF BODY WEIGHT | PER 55 KG OF BODY WEIGHT | PER 75 KG OF BODY WEIGHT |
|---|---|---|---|
| Vitamin E, I.U. | 6–255 | 10–400 | 14–546 |
| Vitamin C, mg | 16–382 | 25–600 | 34–818 |
| Vitamin $B_6$, mg | 13–80 | 20–125 | 27–171 |
| Folic Acid, mg | 0.06–1.9 | 0.1–3.0 | 0.14–4.1 |
| Calcium, mg | 64–636 | 100–1,000 | 136–1,364 |
| Magnesium, mg | 16–255 | 25–400 | 34–546 |
| Linolenic Acid, mg | 6–127 | 10–200 | 14–273 |
| Linoleic Acid, mg | 6–127 | 10–200 | 14–273 |
| Docosahexaenoic Acid, mg | 6–318 | 10–500 | 14–682 |

Tablets incorporating the above formulations are prepared using conventional methods and materials known in the pharmaceutical art. The resulting nutritional conception composition tablets are recovered and stored for future use.

The invention being thus described, it will be apparent that the same may be varied in many ways. Such variations are not to be regarded as a departure from the spirit and scope of the invention, and all such modifications are intended to be within the scope of the appended claims.

We claim:

1. A method for increasing the possibility of conception while enhancing nutritional stores for a developing embryo or fetus prior to and during pregnancy, which comprises:
   administering to an animal during a period commencing prior to at least two weeks before conception a composition comprising:
      about 20 mg to 125 mg per 55 kg of said animal's body weight of a vitamin $B_6$ compound; and
      about 1.0 mg to 3 mg per 55 kg of said animal's body weight of a folic acid compound;
      wherein said composition is specifically formulated to avoid folic acid and vitamin $B_6$ deficiencies associated with infertility and to initiate, stimulate, and act as a catalyst to reactions having a positive impact on the processes of conception and fetal development in order to augment the possibility of conception occurring.

2. The method of claim 1, wherein said animal is of a male gender.

3. The method of claim 1, wherein said animal is of a female gender.

4. The method of claim 1, wherein said nutritional composition is in an oral dosage form.

5. The method of claim 4, wherein said oral dosage form is selected from the group consisting of a chewable tablet, a quick dissolve tablet, an effervescent tablet, a hard gelatin capsule, a soft gelatin capsule, a reconstitutable powder, a suspension, an elixir, a caplet, a health bar, a liquid, a food and combinations thereof.

6. The method of claim 4, wherein said oral dosage form is selected from the group consisting of immediate release, extended release, pulsed release, delayed release, timed release, variable release, controlled release and combinations thereof.

7. The method of claim 1, wherein said nutritional composition is administered once during a twenty four hour period of time.

8. The method of claim 1, wherein said nutritional composition is administered at least twice during a twenty four hour period of time.

9. The method of claim 1, wherein said nutritional composition further comprises a vitamin C compound or derivative thereof in an amount ranging from about 25 mg to 400 mg per 55 kg of said animal's body weight.

10. The method of claim 1, wherein said nutritional composition further comprises a vitamin E compound or derivative thereof in an amount ranging from about 10 mg to 400 mg per 55 kg of said animal's body weight.

11. The method of claim 1, wherein said nutritional composition additionally contains a fertility agent.

12. The method of claim 1, wherein said nutritional composition additionally contains an ovulatory agent.

13. The method of claim 1, wherein said composition is administered about 8 hours prior to sexual intercourse.

14. A method for increasing the possibility of conception while enhancing nutritional stores for a developing embryo or fetus prior to and during pregnancy, which comprises:
   administering to an animal during a period commencing prior to at least two weeks before conception a composition comprising:
      a) about 20 mg to 125 mg per 55 kg of said animal's body weight of a vitamin $B_6$ compound;
      b) about 1.0 mg to 3 mg per 55 kg of said animal's body weight of a folic acid compound; and
      c) about 100 mg to 1,000 mg per 55 kg of said animal's body weight of a calcium compound;
      wherein said composition is specifically formulated to avoid folic acid, calcium, and vitamin $B_6$ deficiencies associated with infertility and to initiate, stimulate, and act as a catalyst to reactions having a positive impact on the processes of conception and fetal development in order to augment the possibility of conception occurring.

15. The method of claim 14, wherein said nutritional composition is administered once during a twenty four hour period of time.

16. The method of claim 14, wherein said nutritional composition is administered at least twice during a twenty four hour period of time.

17. A method for increasing the possibility of conception while enhancing nutritional stores for a developing embryo or fetus prior to and during pregnancy, which comprises:
   administering to an animal during a period commencing prior to at least two weeks before conception a composition comprising:
      about 1.0 mg to 3 mg per 55 kg of said animal's body weight of a folic acid compound; and
      about 100 mg to 1,000 mg per 55 kg of said animal's body weight of a calcium compound;
      wherein said composition is specifically formulated to avoid folic acid and calcium deficiencies associated with infertility and to initiate, stimulate, and act as a catalyst to reactions having a positive impact on the processes of conception and fetal development in order to augment the possibility of conception occurring.

18. The method of claim 17, wherein said nutritional composition is administered once during a twenty four hour period of time.

19. The method of claim 17, wherein said nutritional composition is administered at least twice during a twenty four hour period of time.

* * * * *

UNITED STATES PATENT AND TRADEMARK OFFICE
CERTIFICATE OF CORRECTION

PATENT NO.    : 6,569,857 B1
DATED         : May 27, 2003
INVENTOR(S)   : Hermelin et al.

It is certified that error appears in the above-identified patent and that said Letters Patent is hereby corrected as shown below:

Column 17,
Line 58, change "a health bar" to -- an edible food bar --.

Column 18,
Lines 5-6, after the phrase "vitamin C compound", delete the phrase "or derivative thereof".
Lines 9-10, after the phrase "vitamin E compound", delete the phrase "or derivative thereof".

Signed and Sealed this

Eighteenth Day of November, 2003

JAMES E. ROGAN
*Director of the United States Patent and Trademark Office*